(12) United States Patent
Madiyalakan (10) Patent No.: US 6,716,966 B1
(45) Date of Patent: Apr. 6, 2004

(54) THERAPEUTIC BINDING AGENTS AGAINST MUC-1 ANTIGEN AND METHODS FOR THEIR USE

(75) Inventor: Ragupathy Madiyalakan, Edmonton (CA)

(73) Assignee: AltaRex Corp., Edmonton (CA)

( * ) Notice: Subject to any disclaimer, the term of this patent is extended or adjusted under 35 U.S.C. 154(b) by 0 days.

(21) Appl. No.: 09/641,833

(22) Filed: Aug. 18, 2000

Related U.S. Application Data (60) Provisional application No. 60/164,714, filed on Nov. 11, 1999, and provisional application No. 60/149,492, filed on Aug. 18, 1999.

(51) Int. Cl.$^7$ .............................................. C07K 16/00
(52) U.S. Cl. ............................... 530/387.1; 530/388.1; 530/388.8
(58) Field of Search ................................ 435/325, 344; 530/387.1, 388.1, 388.8

(56) References Cited

FOREIGN PATENT DOCUMENTS

| DE | 195 34 630 | 3/1997 |
|----|-----------|--------|
| WO | WO 93/20841 | 10/1993 |
| WO | WO 94/11508 | 5/1994 |
| WO | WO 97/42973 | 11/1997 |
| WO | WO 99/40881 | 8/1999 |

OTHER PUBLICATIONS

Luo et al., "Molecular Mimicry of Human Tumor Antigen by Heavy Chain CDR3 Sequence of the Anti–Idiotypic Antibody" J. Biochem, vol. 128, No. 3, 2000, pp 345–347.
Price et al, "Summary Report on the ISOBM TD–4 Workshop: Analysis of 56 Monoclonal Antibodies against the MUC1 Mucin" Tumor Biology, vol. 19, No. Suppl. 1, 1998, pp 1–20.
Spencer et al., "Effect of Glycosylation of a Synthetic MUC1 mucin–core–related peptide on recognition by anti–mucin antibodies" Cancer Letters, vol. 100, No. 1/02, 1996, pp 11–15.
Zhenjun et al., "Hypocrellins and Their Use in Photosensitization" Photochemistry and Photobiology, vol. 52, No. 3, 1990, pp 609–616.
Qi W. et al., "Induction of Idiotype Network to Anti–MUC1 Antibody in Breast Cancer" Proceedings of the American Association for Cancer Research Annual, vol. 39, 1998, p 367.

Primary Examiner—Sheela Huff
(74) Attorney, Agent, or Firm—Ropes & Gray LLP (57) ABSTRACT

The invention provides therapeutic compositions comprising binding agents that specifically bind to tumor-associated MUC-1 and reduce, reverse or prevent their effects in cancer. More particularly, the invention provides therapeutic compositions that comprise a binding agent that can specifically bind to an epitope that comprises both peptide and carbohydrate on such tumor-associated MUC-1. The invention further provides methods for the use of such therapeutic compositions in the treatment of cancer.

29 Claims, 6 Drawing Sheets

FIGURE 1

Figure 8-53 SERIES 7: SURVIVAL CURVES IN CB6F1 MICE

```
                       SEQUENCE LISTING

<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: MUC-1 antigen

<400> SEQUENCE: 1

Gly Ser Thr Ala Pro Pro Ala His Gly Val Thr Ser Ala Pro Asp Thr
 1               5                  10                  15

Arg Pro Ala Pro
            20

<210> SEQ ID NO 2
<211> LENGTH: 8
<212> TYPE: PRT
<213> ORGANISM: Artificial Sequence
<220> FEATURE:
<223> OTHER INFORMATION: MUC-1 antigen

<400> SEQUENCE: 2

Ala Pro Asp Thr Arg Pro Ala Pro
 1               5

<210> SEQ ID NO 3
<211> LENGTH: 7
<212> TYPE: PRT
<213> ORGANISM: Artificial Sequence
<220> FEATURE:
<223> OTHER INFORMATION: MUC-1 antigen

<400> SEQUENCE: 3

Ser Ala Pro Asp Thr Arg Pro
 1               5

<210> SEQ ID NO 4
<211> LENGTH: 5
<212> TYPE: PRT
<213> ORGANISM: Artificial Sequence
<220> FEATURE:
<223> OTHER INFORMATION: MUC-1 antigen
```

```
<400> SEQUENCE: 4

Pro Asp Thr Arg Pro
1               5

<210> SEQ ID NO 5
<211> LENGTH: 6
<212> TYPE: PRT
<213> ORGANISM: Artificial Sequence
<220> FEATURE:
<223> OTHER INFORMATION: MUC-1 antigen

<400> SEQUENCE: 5

Asp Thr Arg Pro Ala Pro
1               5
```

THERAPEUTIC BINDING AGENTS AGAINST MUC-1 ANTIGEN AND METHODS FOR THEIR USE

This application claims the benefit of U.S. provisional application No. 60/149,492, filed Aug. 18, 1999, and U.S. provisional application No. 60/164,714, filed Nov. 11, 1999, the entire contents of which are hereby incorporated in reference.

BACKGROUND OF THE INVENTION

1. Field of the Invention

The invention relates to therapeutic compositions for the treatment of cancer. More particularly, the invention relates to the therapeutic treatment of cancers which express the MUC-1 antigen.

2. Summary of the Related Art

The tumor-associated antigen MUC1 is a high-molecular weight glycoprotein that is expressed on many adenocarcinomas. Gendler, et al., J. Biol. Chem. 265:15286, 1990, Gendler, et al., P.N.A.S. U.S.A., 84:6060, 1987, Siddiqui, et al., P.N.A.S. U.S.A. 85:2320, 1988, and Ligtenberg, et al., J. Biol. Chem. 265:5573, 1990 teach that the extracellular domain of the integral membrane glycoprotein consists mainly of 30 to 90 tandem repeats of a 20 amino acid core sequence that is rich in serine, threonine and proline, GSTAPPAHGVTSAPDTRPAP (SEQ ID NO:1). Burchell, et al., Cancer Surv. 18:135, 1993, teaches that the number of repeats expressed by an individual is genetically determined, resulting in size polymorphism.

Price, et al. Breast 2:3, 1993, teaches that the minimum sequence recognition of most MUC1 reactive monoclonal antibodies all lie within APDTRPAP (SEQ ID NO:2), which is believed to be a type 1 β-turn. Burchell, et al. Cancer Surv. 18:135, 1993, discloses that the sequence SAPDTRP (SEQ ID NO:3) in the MUC1 tandem repeat is an immunodominant B cell epitope and that a T cell epitope of the tandem repeat has been mapped to the pentamer, PDTRP (SEQ ID NO:4). Adjacent amino acids and sugar residues may play an important role in the binding in the native molecule. A large number of tandem repeats may be present in the MUC1 mucin, ranging between 30 and 90 per molecule.

Tumor MUC-1 are generally hypoglycosylated and the glycosylation sites often have aberrant sugar chain extensions. Magnani, et al., Cancer Res. 43:5489, 1983, teaches that this aberrant glycosylation results in the exposure of normally cryptic peptide epitopes and the creation of novel carbohydrate epitopes. Because of their high molecular weight ($2\times10^5$–$5\times10^7$ dalton) as well as extensive glycosylation, cell membrane mucins exist as flexible rods and protrude at a relatively great distance from the cell surface. Mucins thus form an important component of the glycocalyx and are probably the first point of cellular contact with antibodies and cells of the immune system.

Rittenhouse, et al., Lab. Med. 16:556, 1985; Price, et al., Breast 2:3, 1993; Metzgar, et al., P.N.A.S. U.S.A. 81:5242, 1984; Magnani, et al., Cancer Res. 43:5489, 1983; Burchell, et al., Int. J. Cancer 34:763, 1984; Linsley, et al., Cancer Res. 46:5444, 1986; and Neutra, et al., in *Physiology of the Gastrointestinal Tract*, Johnson, L. R. ed., 2 edition, Raven Press, New York, p 975–1009, 1987, teach that normal tissue mucins are usually only displayed and secreted on the apical surfaces of epithelial cells, specifically, the mucosal surfaces. Ho, et al., Cancer Res. 53:641, 1993, teaches that the MUC1 mucin is highly expressed on the apical membranes of bronchus, breast, salivary gland, pancreas, prostate, and uterus, and sparingly expressed on gastric surface cells, gall bladder, small intestine and colonic epithelium. Cell surface MUC-1 may serve important functions, including protection against proteolytic degradation and providing a barrier against microbial toxins. Jentoff, Trends Biol. Sci. 15:291, 1990; Parry, et al., Exp. Cell Res. 188:302, 1990; Wong, et al., J. Immunol. 144:1455, 1990; Devine and Mackenzie, BioEssays 14:619, 1993 teach that they can also serve as lubrication for epithelial surfaces, presentation of carbohydrate receptors for micro-organisms to assist in their elimination, for selection of symbiotic strains in competition with pathogens, for transmembrane signal-transduction, cell-cell interactions, regulation of cell growth, as well as maintenance of polarity.

Tumor mucins are thought to serve a critical function for tumor survival in the body. They may protect tumor cells from the low pH caused by high metabolic activity within the tumor. MUC1 is thought to inhibit tumor cells from forming tight aggregates with the tumor tissue thereby increasing metastatic potential. Regimbald et al., Cancer Res. 56:4244, 1996, teaches that MUC1 is involved in the homing of circulating tumor cells to distant sites by its molecular interaction with ICAM1 present on normal cells.

Mucins may also protect tumor cells from recognition by the immune system. Devine and MacKenzie, BioEssays 14:619, 1993, teaches that when MUC-1 are shed into the circulation, they may play a role in the observed tumor-specific immune-suppression possibly by providing steric hindrance to cell surface antigens to cellular and humoral immune effectors. Codington, et al., in *Biomembranes*, Mansoe, L. A., ed., Plenum Pub. Corp, New York, pp 207–259, 1983; Miller, et al., J. Cell Biol. 72:511, 1977; Hull, et al., Cancer Commun. 1:261, 1989, teach that cell membrane MUC-1 can mask other cell-surface antigens and protect cancer cells from immune attack.

Rising concentrations of tumor-associated MUC-1 in the patient's serum have also been correlated with increasing tumor burdens indicating progression of disease. Price et al., Breast 2:3, 1993 and Pihl et al., Pathol. 12:439, 1980, teach that high serum levels of MUC-1 are correlated with poor prognosis in cancer patients.

There is, therefore, a need for new therapeutic compositions which can selectively bind tumor-associated MUC-1 and reduce, reverse or prevent their effects in cancer. Kufe, U.S. Pat. No. 5,506,343, 1996, teaches that tumor-associated MUC-1 antibody specificity can only be achieved when fully unglycosylated peptide is recognized by the antibody. Unfortunately, however, this antibody has not been shown to be therapeutically effective against a tumor that expresses a tumor-associated MUC-1. While tumor-associated MUC-1 has reduced and altered glycosylation, they still retain carbohydrate structures specific for the cancer. There is, therefore, a particular need for a therapeutic composition that comprises a binding agent that can bind to an epitope of a MUC-1 that includes both peptide and tumor specific carbohydrate.

BRIEF SUMMARY OF THE INVENTION

The invention provides therapeutic compositions comprising binding agents that specifically bind to tumor-associated MUC-1 and reduce, reverse or prevent their effects in cancer. More particularly, the invention provides therapeutic compositions that comprise a binding agent that can specifically bind to an epitope that comprises both peptide and carbohydrate on such tumor-associated MUC-1.

The invention further provides methods for the use of such therapeutic compositions in the treatment of cancer. The present inventors have surprisingly discovered that the relative specificity for tumor associated MUC-1 is not necessarily sacrificed in the case of binding agents that recognize an epitope that includes carbohydrate. The compositions and methods according to the invention provide new promise for therapeutic treatment of tumors that produce tumor-associated MUC-1 antigens.

In a first aspect, the invention provides therapeutic compositions comprising binding agents that specifically bind to tumor-associated MUC-1 and that are effective in reducing tumor burden or prolonging survival in a mammal having a tumor that expresses a tumor-associated MUC-1. In certain preferred embodiments, the MUC-1 is human MUC-1. Preferred binding agents bind specifically to MUC-1 epitopes that include carbohydrate. Particularly preferred binding agents include peptides or peptidomimetics, including antibodies and antibody derivatives.

In a second aspect, the invention provides methods for therapeutically treating a mammal bearing a tumor that comprises tumor-associated MUC-1 antigen. The methods according to this aspect of the invention comprise administering to the mammal an effective amount of a binding agent according to the invention. Preferably, the binding agent is administered intravenously or subcutaneously at low dosages.

DETAILED DESCRIPTION OF THE PREFERRED EMBODIMENTS

The invention relates to therapeutic compositions for the treatment of cancer. More particularly, the invention relates to the therapeutic treatment of cancers which express the MUC-1 antigen. The patents and publications recited herein reflect the knowledge in this field and are hereby incorporated by reference in their entirety. In case of conflict between the teachings of any of these references and the present specification, the latter shall prevail.

The invention provides therapeutic compositions comprising binding agents that specifically bind to an epitope of tumor-associated MUC-1 and reduce, reverse or prevent their effects in cancer. More particularly, the invention provides therapeutic compositions that comprise a binding agent that can specifically bind to an epitope that comprises both peptide and carbohydrate on such tumor-associated MUC-1. The invention further provides methods for the use of such therapeutic compositions in the treatment of cancer. The compositions and methods according to the invention provide new promise for therapeutic treatment of tumors that produce tumor-associated MUC-1 antigens.

In a first aspect, the invention provides therapeutic compositions comprising binding agents that specifically bind to tumor-associated MUC-1 and that are effective in therapeutically treating a mammal having a tumor that expresses a tumor-associated MUC-1. In certain preferred embodiments, the MUC-1 is human MUC-1. As used herein, the term "therapeutically treat" or "therapeutically treating" means causing statistically significant reduction in tumor volume, or causing statistically significant prolongation of survival in the mammal bearing the tumor. A "binding agent" is a molecule or macromolecule which binds under physiological conditions to MUC-1 and inhibits its biological activity. "Specifically binds" and "binds under physiological conditions" mean forming a covalent or non-covalent association with an affinity of at least $10^6 M^{-1}$, most preferably at least $10^9 M^{-1}$, either in the body, or under conditions which approximate physiological conditions with respect to ionic strength, e.g., 140 mM NaCl, 5 mM $MgCl_2$. As a practical matter, such binding in the body may be inferred from reduction of tumor burden or prolonged survival. In preferred embodiments, the binding agent specifically binds an epitope that contains an immunological determinant that includes carbohydrate. Tumor MUC-1 are generally hypoglycosylated and the glycosylation sites are filled with aberrant sugar chain extensions, thus, distinguishing normal from tumor MUC-1. Aberrant glycosylation results in the exposure of normally cryptic peptide epitopes and the creation of novel carbohydrate epitopes. Preferred binding agents according to the invention can bind to these novel epitopes. An "epitope" is a portion of an antigen which is bound under physiological conditions by a binding agent according to the invention. An "immunological determinant" is a three-dimensional shape which contributes to the overall three-dimensional shape of an epitope. In preferred embodiments, the binding agent binds to an epitope that comprises immunological determinants from amino acid residues of a peptide having the amino acid sequence DTRPARP (SEQ ID NO:5). An "amino acid residue" is an amino acid as it is in place in a particular peptide. "Inhibition of biological activity", as used herein, means a statistically significant reduction in tumor burden, or a statistically significant prolongation of survival in an animal or patient bearing a tumor. Such statistically significant inhibition is illustrated in the examples hereof. Certain preferred embodiments of binding agents according to the invention are non-radiolabeled. Certain binding agents according to the invention bind to both circulating and tumor-bound tumor-associated MUC-1, wherein "tumor-associated" refers to the altered glycosylation of MUC-1 made by tumor cells, rather than to its proximity to a tumor. A particularly preferred binding agent is Alt-1 (ATTC Patent Deposit Designation PTA-975).

A cell line which produces the monoclonal antibody Alt-1 was deposited on Nov. 23, 1999, at the American Tissue Culture Collection, 10801 University Blvd., Manassas, Va. 20110-2209, and was given the ATCC accession number PTA-975. Alt-1 will be maintained under the conditions of the Budapest Treaty. All restrictions upon public access to the deposited material will be irrevocably removed upon the grant of a patent of this application.

Preferred tumors for treatment include, without limitation, breast carcinoma, colon carcinoma, esophageal squamous cell carcinoma, pancreatic carcinoma, prostate carcinoma and multiple myeloma.

Preferably, the binding agent according to the invention is a peptide or a peptidomimetic. For purposes of the invention, a "peptide" is a molecule comprised of a linear array of amino acid residues connected to each other in the linear array by peptide bonds. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above.

In certain preferred embodiments, such a binding agent comprises a complementarity determining region of an antibody which binds under physiological conditions to a MUC-1 epitope that includes carbohydrate, or a peptidomimetic of such a complementarity-determining region. For purposes of the invention, a "complementarity determining region" (CDR) of an antibody is that portion of an antibody which binds under physiological conditions to an epitope, including any framework regions necessary for such binding, and which is preferably comprised of a subset of amino acid residues encoded by the human heavy chain V, D and J regions, the human light chain V and J regions, and/or combinations thereof. Certain preferred antibodies are xenogeneic antibodies, i.e. they are from a species that is different from the species being administered the antibody. Such antibodies will cause human anti-xenogeneic antibodies (HAXA) to be elicited. Preferred antibodies include murine antibodies, which elicit a human anti-mouse antibody (HAMA) response.

Those skilled in the art will recognize that, given the antibody disclosed herein, those skilled in the art are enabled to make a variety of antibody derivatives. For example, Jones et al., Nature 321: 522–525 (1986) discloses replacing the CDRs of a human antibody with those from a mouse antibody. Marx, Science 229: 455–456 (1985) discusses chimeric antibodies having mouse variable regions and human constant regions. Rodwell, Nature 342: 99–100 (1989) discusses lower molecular weight recognition elements derived from antibody CDR information. Clackson, Br. J. Rheumatol. 3052: 36–39 (1991) discusses genetically engineered monoclonal antibodies, including Fv fragment derivatives, single chain antibodies, fusion proteins chimeric antibodies and humanized rodent antibodies. Reichman et al., Nature 332:323–327 (1988) discloses a human antibody on which rat hypervariable regions have been grafted. Verhoeyen, et al., Science 239:1534–1536 (1988) teaches grafting of a mouse antigen binding site onto a human antibody.

In addition, given the antibody disclosed herein, those skilled in the art are enabled to design and produce peptidomimetics having binding characteristics similar or superior to such complementarity determining region (see e.g., Horwell et al., Bioorg. Med. Chem. 4:1573 (1996); Liskamp et al., Recl. Trav. Chim. Pays- Bas 1:113 (1994); Gante et al., Angew. Chem. Int. Ed. Engl. 33: 1699 (1994); Seebach et al., Helv. Chim. Acta 79:913 (1996)). Accordingly, all such antibody derivatives and peptidomimetics thereof are contemplated to be within the scope of the present invention. Compositions according to the invention may further include physiologically acceptable diluents, stabilizing agents, localizing agents or buffers.

In some preferred embodiments, the binding agents according to the invention are activated, preferably by chemical or photodynamic approaches. Preferred chemical approaches include organic reducing agents, such as formamidine sulfonic acid, inorganic reducing agents, such as mercurous ion, stannous ion, cyanide ion, sodium cyanoborohydride and sodium borohydride, thiol exchange reagents, such as dithiothreitol, mercaptoethanol and mercaptoethanolamine, and protein reducing agents, such as thioredoxin. Use of these reagents results in reduction of some disulfides within the binding agent to produce a binding agent having some sulfhydryl groups. The presence of such groups can change the tertiary structure of the binding agent. Such structural change can modulate the immunoreactivity of the binding agent. Such modulation may lead to an improved anti-idiotypic response and/or cellular response in an individual to whom the binding agent is administered.

In some embodiments, activation utilizes a photodynamic approach. See, e.g., international application PCT/US93/06388. The binding agent is preferably irradiated with ultraviolet radiation, preferably in the spectrum range of from about 10 to about 820 nm. More preferably, at least 90% and most preferably at least 99% of the radiation is in the spectrum range of 250 to 320 nm. Such UV radiation is conveniently supplied from a source such as a hydrogen or deuterium discharge lamp, a xenon arc lamp, or a mercury vapor lamp.

Conventional filters may be employed to obtain optimum spectrum wavelengths. (See e.g., *Photochemistry*, pp. 686–798 (John Wiley & Sons, N.Y., 1966).

In some preferred embodiments, the binding agents according to the invention may optionally be coupled to photodynamic agents. Preferably, such coupling is by covalent linkage or by liposomal association. Liposomal association is preferably achieved by mixing the photodynamic agent with a binding agent in the presence of a liposome-forming reagent. In certain preferred embodiments, the binding agent according to the invention is covalently linked to the liposome-forming reagent. Preferred photodynamic agents include hypocrellins.

In some preferred embodiments, the binding agents according to the invention specifically exclude the following monoclonal antibodies: HMPV, VU3-C6, MF06, VU-11-D1, MF30, BCP8, DF3, BC2, B27.29, VU-3-D1, 7540MR, MF11, Bc4E549, VU-11-E2, M38, E29, GP1.4, 214 D4, BC4W154, HMFG-1, HMFG-2, C595, Mc5 and A76-A/C7. Each of these names are as used in the literature relating to anti-MUC-1 antibodies.

Without wishing to be bound by theory, it is believed that certain binding agents of the present invention act through a mechanism that generally includes an anti-idiotype network. In addition to the induction of an anti-idiotype network, the administration of binding agents according to the invention leads to the formation of complexes with MUC-1, which is postulated to elicit a more effective presentation of the antigen to the immune system. The complex formation between antigen and antibody can have several effects. Preferred binding agents according to the invention can bind both circulating and cellular MUC-1 tumor-associated antigen. Thus, the possible immune suppressive effect of the MUC-1 antigen can be inactivated by removal of the complex from circulation. The complex between antigen and antibody can be directed to antigen-presenting cells, carrying Fc receptors or membrane Ig receptors (macrophages, dendritic cells, B cells). The enhanced uptake of antigen by specific antigen-presenting cells will lead to increased presentation of antigen-derived peptides to T cells. The complex formation between antigen and antibody can also change the way the antigen is processed within the antigen-presenting cell, exposing novel immune dormant or cryptic epitopes, thus overcoming tolerance to the tumor-associated antigen. Because the binding agents according to the invention bind an epitope that is at least partially carbohydrate, they may also act to inhibit immune suppression by preventing interaction of the carbohydrate of lectin receptors on T cells. Of course, the embodiments of binding agents according to the invention that are coupled to photodynamic agents can also act through direct cytotoxicity to the tumor cells.

Thus, in a second aspect, the invention provides methods for therapeutically treating a mammal bearing a tumor that comprises tumor-associated MUC-1 antigen. The methods according to this aspect of the invention comprise administering to the mammal an effective amount of a binding agent according to the invention. Preferably, the binding agent is a peptide, or a peptidomimetic, most preferably an antibody or antibody derivative, or a peptidomimetic thereof. Preferably, the mammal is a human. The binding agent is preferably administered parenterally, more preferably intravenously or subcutaneously. In certain preferred embodiments, intravenous injection is carried out in the absence of any adjuvant. In certain preferred embodiments, the binding agent is administered subcutaneously in the presence of an adjuvant, such as RIBI. In certain embodiments, the binding agent is covalently linked to an immunogenic carrier molecule, such as KLH or xenogeneic immunoglobulin. In certain preferred embodiments, the method according to the invention utilizes binding agents that are non-radiolabeled. Certain preferred embodiments of the method according to the invention utilize binding agents that bind to both circulating and tumor-bound tumor-associated MUC-1, wherein "tumor-associated" refers to the altered glycosylation of MUC-1 made by tumor cells, rather than to its proximity to a tumor.

Preferably, the binding agents are administered at a dosage of less than about 8 mg/30 kg body weight, preferably less than about 3 mg/30 kg body weight, more preferably from about 0.5 to about 2 mg/30 kg body weight, still more preferably from about 0.5 to about 1.5 mg/30 kg body weight, and most preferably at about 1 mg/30 kg body weight. In certain embodiments, the dosage will be the maximum amount of binding agent that does not induce antibody-mediated toxicity. In certain embodiments, the dosage will be the maximum amount of binding agent that does not produce ADCC OR CDC. In these embodiments, ADCC is assessed by incubating $^{51}$Cr-labeled tumor cells with a binding agent according to the invention and adding fresh human PBMCs, followed by incubation for 4 hours and measurement of specific lysis. ADCC is deemed to be absent if specific lysis is less than 15%. "Antibody-mediated toxicity" means clinical toxicity, such as abnormal serum chemistries, impaired renal function, signs and symptoms of serum sickness or anaphylaxis. In certain embodiments a single such dosage will therapeutically treat the mammal. In other embodiments, treatment may be ongoing, e.g., four times per year for three or more years.

The term "effective amount" means an amount sufficient to therapeutically treat the mammal. The terms "therapeutically treat", "therapeutically treating", "binding agent", "peptide", "peptidomimetic", "antibody" and "antibody derivative" are all used as described for the first aspect of the invention.

The following examples are intended to further illustrate certain preferred embodiments of the invention, and are not to be construed as narrowing the scope of the invention. The binding agent used in the following examples is Alt1, unless otherwise specifically stated.

EXAMPLE 1

Generation of a Hybridoma to Produce a Binding Agent

A binding agent was prepared for use in the immunotherapy of patients with tumors expressing the tumor associated antigen (TAA) known as MUC1 (Taylor-Papadimitriou. Int. J. Cancer 49:1, 1990). The binding agent is an activated murine monoclonal antibody (MAb), an $IgG_{1k}$ subclass immunoglobulin. The binding agent binds with high affinity to MUC1, a high molecular weight glycoprotein that is expressed on many tumors (Ho, et al. Cancer Res. 53:641, 1993). The binding agent specifically recognizes the sequence DTRPAP within the MUC1 tandem repeat peptide sequence. This binding agent is referred to as Alt-1. The murine cell line or hybridoma that secretes the binding agent was generated by immunizing mice with MUC1 and harvesting and immortalizing the antibody-secreting splenocytes. The steps involved in development of the hybridoma included (a) the immunization of BALB/cCrAltBM female mice with MUC1 from several sources; (b) harvesting the splenocytes from the mice, (c) and immortalizing the splenocytes by fusing them with the myeloma cell line SP2/0-Ag14, (d) screening and selection of the desired clone by assaying the secreted antibodies for ability to bind MUC1, (e) expansion of the selected clone in the appropriate media, (f) isotype switching of the clone from an IgM to an IgG, and (g) continued 0.2 µm filtration and dilution using formulation buffer (10 mM sodium pyrophosphate-HCl, pH 8.0). Specific binding of the binding agent to MUC1 expressing breast cancer cells and MUC1 transformed murine cells was demonstrated by FACS, fluorescence microscopy and other binding assays.

EXAMPLE 2

Purification, Preparation Activation and Formulation of a Binding Agent

Growth media was collected from the hybridoma according to Example 1. The binding agent was purified from the growth media by (a) clarification of the growth medium by microfiltration using a 0.22 µm filter, (b) anion exchange chromatography on Q Sepharose® FF (Amersham Pharmacia Biotech) in 50 mM Tris, pH 8.0 with a NaCl gradient from 40 mM at equilibrium to 130 mM at elution, This was followed by 0.22 µm microfiltration, (c) affinity chromatography on Protein A Sepharose® FF (Amersham Pharmacia Biotech) with elution occurring after change in buffer from 1.0 M glycine, 3.0 M NaCl, pH 8.8 for equilibration to elution buffer containing 200 mM glycine, 150 mM NaCl, pH 2.8, (d) incubation at pH 3.5 for 40 minutes, (e) nanometer filtration on Viresolve filter (Millipore Corporation), followed by 0.22 µm microfiltration, (e) concentration and diafiltration by tangential flow ultrafiltration using a 50 kD NMWCO Biomax membrane (Millipore Corporation) followed by 0.22 µm microfiltration. Purified binding agent was then activated in the following manner. Bulk fluid of purified binding agent (5 mg/ml in low molarity phosphate, pH 5–10) was exposed, compounded with excipient (stannous chloride) and reducing agent (sodium pyrophosphate) to 200–400 nm radiation, 90% at 300 nm +/−20 nm from eight lamps at 3–9 watts per lamp to yield activated binding agent. The activated binding agent was supplied in vials containing 2 mg of the activated binding agent in frozen or lyophilized form together with the same reducing agent and buffer complex. Preparation of the final formulation was performed under aseptic conditions not more than 4 hours prior to the administration of the binding agent. The binding agent was prepared by the following procedure using aseptic methods. We folded back the metal tab on the top of the binding agent vial and swabbed the rubber septum with alcohol. In a suitable syringe, was drawn up 2.0 mL of Sodium Chloride Injection USP and it was added to the vial. We mixed the vial contents by gently swirling the vial to form the binding agent solution. We did not mix vigorously as this may result in the formation of foam. We noted the clock time immediately after this step. The vial was examined to ensure that the solution was free of foreign or particulate matter.

EXAMPLE 3

Reaction of a Binding Agent With Normal and Tumor Tissues

The tissue reactivity of a binding agent according to Example 2 was tested by immunohistochemical procedures using the avidin-biotin amplified immunoperoxidase technique of staining frozen tissues. In a preliminary study, the binding agent was used to examine the expression and distribution of the MUC1 antigen in a selected panel of normal human tissues and human tumors and to determine the optimal concentration of antibody or final product for specific staining of MUC1-expressing tissues. Specific staining was observed in tumor cells of breast, colon and lung as well as in epithelial cells of normal breast, kidney, large intestine and lung. In a second study, the binding and distribution of the binding agent to a broader panel of normal human tissues and human tumors was performed using an isotype-matched antibody (MOPC-21) as a control. Specific staining with the binding agent was noted in breast carcinoma, colon carcinoma, esophageal squamous cell carcinoma, pancreatic carcinoma and prostate carcinoma. Some specific staining was also observed in melanomas and sarcomas. Staining with the binding agent was also observed in some normal human tissues and was primarily localized to epithelial cells. These results are consistent with literature reports on the expression of MUC1 peptide and MUC1 mRNA in normal human tissues and human tumors, and demonstrate the reactivity of a binding agent according to the invention to these tissues.

EXAMPLE 4

Generation of an Anti-idiotype Response

The binding agent of Example 2 possesses variable regions specific for antigen (MUC1) recognition known as idiotypes. These variable regions are themselves immunogenic and can generate a series of anti-idiotypic antibodies known as Ab2. Some of these Ab2 can effectively mimic the three-dimensional structure or the peptide sequence of the original antigen (MUC1) and can be used to generate specific immune responses similar to those induced by the original antigen. Accordingly, administration of the binding agent is expected to generate antigen mimics or internal image antibodies in the form of Ab2, which can generate the specific anti-MUC1 immune response. To demonstrate the induction of Ab2 by the binding agent, BALB/c mice were immunized with binding agent conjugated to KLH (Keyhole Limpet Hemocyanin), in combination with RAS adjuvant (RIBI Adjuvant System). KLH and the adjuvant were included in these experiments to enhance the normally weak immune response in a mouse to a mouse antibody (as antigen). An isotype-matched antibody served as a control. After each of six injections (alternating between intraperitoneal and subcutaneous administration), sera were analyzed in a sandwich assay using F(ab')$_2$ fragments of binding agent on the solid phase. Bound murine antibodies were detected by goat anti-mouse IgG-(F$_c$-specific)-HRP as a tracer. Injection of binding agent conjugated to KLH did result in the production of anti-idiotypic antibody (Ab2) that was greater than an isotype-matched control MAb. A minimum of four injections at a dose of 50 µg/mouse (0.83 mg/m$^2$) was required to induce a measurable humoral response. In order to demonstrate that the anti-binding agent (Ab2) in the serum was of the type Ab2(β), the binding to binding agent was tested in the presence of MUC1. This binding was inhibited by the presence of MUC1 as would be expected for an Ab2(β) type antibody. Ab3 antibodies were measured in the serum samples by using a MUC1 ELISA. Anti-anti-idiotypic antibodies (Ab3) could be detected in the sera of mice immunized with binding agent versus the control sera. Similar to the Ab2 levels, the Ab3 levels reached their peak after six injections. In addition, a murine monoclonal Ab2 generated against binding agent was used in turn to generate anti-anti-idiotypic (Ab3) antibodies in rats. Two out of the three rats thus immunized demonstrated positive binding to the murine monoclonal Ab2. Generation of anti-MUC1 antibodies in a different species was considered to be an important criterion for classification of an Ab2β, in addition to the ability to inhibit the binding between Ab1 and Ab2 by the nominal antigen, i.e. MUC1.

EXAMPLE 5

Induction of a Cellular Response

T cell proliferation studies showed a specific response to the injected binding agent according to Example 2 and MUC1, indicating the presence of idiotype-specific T cells (T2) and anti-idiotype-specific T cells (T3). In addition, the murine monoclonal Ab2 was also evaluated for its ability to be recognized by MUC1-specific T cells. The proliferation of such T cells in response to Ab2 was monitored by $^3$H-Thymidine uptake and compared to MUC1. The assay was performed as a $^3$H-Thymidine uptake study. Spleens were removed from each group of immunized mice and the lymphocytes were separated from red blood cells on Histopaque 1077 (Sigma). Cells were seeded at a concentration of 2×10$^5$ cells/well in 100 µL of AIM-V serum free medium (Gibco) into a 96-well U-bottomed plate (Becton Dickinson). The stimulants were added in triplicate and incubated with the cells for 3 days. The cells were pulsed with 1 µCi [$^3$H-methyl] Thymidine per well for 24 hours. The cells were harvested in a cell harvester (Skatron) and the radioactivity assayed in a beta counter (Beckman). Stimulators included MUC-1, MUC-1 peptide, anti-MUC-1 antibodies, control antibodies and phytohemagglutinin (PHA). Ab2 and MUC1 show similar reactivity providing further evidence of the cellular immune response.

EXAMPLE 6

Determination of Dose Regimen

The dose response of binding agent according to Example 2 for the development of rat anti-murine antibodies (RtAMA) and rat anti-idiotypic antibodies (Ab2) was investigated in normal rats. Male Sprague-Dawley rats were immunized with binding agent at doses ranging from 26 µg to 213 µg by intravenous administration and one dose at 106 µg by subcutaneous administration. Immunizations were performed five times at intervals of 2 weeks. Baseline and test serum samples (one week following injection) were obtained from each rat. Two ELISA assays were developed to measure RtAMA and Ab2. The RtAMA ELISA measures the amount of antibody that binds to the constant region of a Mouse IgG1 antibody. The Ab2 ELISA measures the amount of antibody reactive with the binding region of the binding agent. A dose of 53 µg (1.3 mg/m$^2$), appeared to be optimal in inducing RtAMA via intravenous injection. Injection of the antibody subcutaneously with adjuvant induced much stronger responses, three times higher than the same dose injected intravenously and two times higher than the most effective intravenous dose (1.3 mg/m$^2$). A dose of 1.3 mg/m$^2$ induced a persistent RtAMA response. Higher doses seem to induce anergy, since the response decreased with increasing number of injections at 2.6 mg/m$^2$ and no response was obtained with the highest dose tested (5.2 mg/m$^2$). Binding agent also induced an anti-idiotypic response, however, the response was not proportional to the dose injected. It was observed that the same dose effective for RtAMA was also the optimum dose for induction of anti-idiotypic antibodies. In the intravenous dosing schedule, a dose of 1.3 mg/m$^2$ was the only dose effective in inducing a strong Ab2 response. Using a subcutaneous injection of the antibody produced a better response, with a subcutaneous dose of 2.6 mg/m$^3$ inducing the strongest Ab2 response overall. Overall, correlation was observed between the RtAMA and Ab2 responses, showing optimum responses for the same intravenously administered doses. However, the absolute amounts of Ab2 and RtAMA cannot be directly compared. It appears that a dose of 1.3 mg/m$^2$ (equivalent to approximately 2 mg/60 kg patient) is optimal to induce a humoral response after intravenous injection of binding agent. RtAMA could be detected as early as week 6 after the first immunization and Ab2 at week 4 (subcutaneous immunization) or week 10 (intravenous immunization). The intravenous route required more immunizations to induce an immune response than the subcutaneous route. This weaker immune response may be due to the reduced immunogenicity of mouse proteins in this related species, rats. From these experiments, it appears that the suggested dose for therapeutic treatment is about 2 mg per patient, not taking into account any effect of circulating antigen on the immune response.

EXAMPLE 7

Confirmation of Dose Regimen

Similar to the study performed in rats, a dose escalation study was performed to investigate the dose required to induce an immune response in rabbits. Rabbits were used to more closely approximate the response seen in humans (recognition as foreign) to murine MAbs than either rats or mice. Rabbits were immunized with various amounts of the antibody and serum samples were analyzed for Ab2 and Rabbit-Anti Mouse Antibodies (RAMA). Female New Zealand White rabbits were immunized with binding agent according to Example 2 at three dose levels (125, 250 and 500 μg) by intravenous administration and one dose (125 μg) by subcutaneous administration. Baseline and test serum samples (obtained approximately every 2 weeks) were obtained from each rabbit. Two ELISA assays were developed to measure RAMA and Ab2. The RAMA ELISA measures the amount of antibody that binds to the constant region of a Mouse IgG1 antibody. The Ab2 ELISA measures the amount of antibody reactive with the binding region of the binding agent. The RAMA response represents the humoral response of the host to the constant regions of the injected murine antibody. A dose of 0.575 mg/m$^2$ was injected subcutaneously as a positive control. Three different doses were injected intravenously: 0.575, 1.15 and 2.3 mg/m$^2$. The RAMA response was strongest in rabbits injected intravenously with 250 μg/rabbit of MAb-ALT-1, followed by the subcutaneous injection of 125 μg/rabbit, the intravenous injection of 500 μg/rabbit and the intravenous injection of 125 μg/rabbit. The binding agent induced an immune response in rabbits as both Ab2 and RAMA were found in samples from the first to last bleed. A dose of 250 μg/rabbit (1.15 mg/m$^2$, equivalent to 2 mg/60 kg patient) induced the highest responses for both types of antibody, Ab2 and RAMA. The induced Ab2 could be inhibited by MUC1 but not the MUC1 peptide or CA19.9. The binding agent also induced an anti-idiotypic response in rabbits; however, the Ab2 response was not directly correlated with the dose injected. It was observed that a dose of 250 μg/rabbit gave the highest Ab2 response of the three intravenously administered doses. Subcutaneous injection of the antibody at 125 μg/rabbit induced the strongest Ab2 response overall. The induced Ab2 competed with MUC1 but not the MUC1 peptide at the concentrations examined. It is interesting to note that the route of administration affects the type of immune response. The Ab2 response was strongest in subcutaneously immunized rabbits, whereas the general RAMA response was best in rabbits injected intravenously. Overall, the RAMA and Ab2 responses correlated, showing optimum responses for the same intravenously administered doses. These results demonstrate that a dose of 1.15 mg/m$^2$ (equivalent to 2 mg/60 kg patient) was optimal to induce a humoral response after the intravenous injection of MAb-ALT-1. RAMA and Ab2 could be detected as early as week 2 after the first immunization. Therefore, the immune response in rabbits was superior to the antibody response in rats (detection at week 8 for intravenous administration). Therefore, from these experiments, the suggested dose for therapeutic treatment is about 2 mg per 60 kg patient, not taking into account any effect of circulating antigen on the immune response.

EXAMPLE 8

Initial Tumor Treatment Studies

Tumor cells used in the animal model should have both host compatibility and MUC1 expression. Only a MUC1 gene transfected mouse tumor cell line qualifies as a model in mice. Two MUC1 transfectoma cell lines, MT and 413BCR were evaluated. Both of these cell lines are derived from the mouse mammary carcinoma cell line 410.4 and were transfected with the full length MUC1 gene containing more than 20 tandem repeat epitopes. Both cell lines are compatible with BALB/c and CBGF1 mice. These cell lines highly express the MUC1 antigen as analyzed by binding of binding agent according to Example 2 to these cells by FACS analysis. MT cells were injected intravenously into CB6F1 mice and implanted in the lungs. Tumor foci appeared in the lungs 30–40 days after injection and the mice died at 50–60 days without treatment. Histopathological analysis also confirmed tumor in the lung and MUC1 expression on the tumor tissue. This cell line does not form tumors subcutaneously, even when injected at a relatively high concentration of 2×10$^7$ cells per mouse. With 413BCR cells, BALB/c mice were injected subcutaneously in the flank or mammary fat pad at various cell concentrations (2.5–5×10$^6$ cells per mouse). Tumors developed within 10–15 days and there was a lower rejection rate when the tumors were transplanted into the mammary fat pad. For therapeutic studies, tumors were measured for tumor volume according to the formula: $(a \times b^2)/2$, where a represents the longest diameter and b represents the shortest diameter. To verify MUC1 expression of the transfectoma in vivo, MT tumor-bearing mice were sacrificed and the lungs were aseptically removed. The tumor tissue was removed from the lungs, cut into small pieces and digested with trypsin for 10 minutes. The tumor cells were then cultured for three days and FACS analysis was performed. The results indicated that more than 80% of the MT transfectoma cells were expressing the MUC1 antigen after 1 month of growth in vivo. The binding ability of the antibody-KLH conjugate (KLH was used to increase the immunogenicity of the murine antibody in mice) to the MUC1 antigen was measured by two methods, ELISA and RIA, and demonstrated the ability of the immunogens to recognize their targets in vivo. Two different types of adjuvants, RAS (RIBI Adjuvant System) and Quil A were employed in these studies. RAS is a stable oil-in-water emulsion containing highly purified bacterial components from *Mycobacterium tuberculosis*, the organism that is the major component in Freund's Complete Adjuvant (FCA). Quil A is a surface-active agent used as an alternative but can only be injected subcutaneously. Both adjuvants were used in separate experiments. Serum samples obtained throughout the experiments were analyzed by ELISA for Ab2 and/or Ab3 content. A lymphocyte proliferation assay was performed by determination of $^3$H-Thymidine uptake by a standard protocol using lymphocytes isolated from the spleens of immunized mice. Stimulants included MUC1, MUC1 peptide, anti-MUC1 antibodies, control antibodies and phytohemagglutinin (PHA). At the end of each experiment with CB6F1 mice, animals were sacrificed and the number of tumor foci in the lungs was analyzed by a direct counting technique. Additionally, in a select group of mice, $^{125}$I-deoxy-Uridine was injected into the mice 4 hours prior to animal termination. The lungs were assayed for radioactivity in a gamma counter to enumerate tumor burden. The immune responses and efficacy of binding agent, binding agent-KLH, binding agent-hIgG and binding agent-MUC1 complex were analyzed in both tumor-bearing BALB/c and tumor-bearing CB6F1 mice.

The first series of experiments evaluated the effect of a conjugate of binding agent according to Example 2 (KLH) or a complex (binding agent MUC1) on the induction of a humoral response (anti-mouse antibody, Ab2 and Ab3), a cellular response (T cell proliferation) as well as the effect of these compounds on tumor growth and/or size. Mice were implanted with 413BCR tumor cells 2 weeks after the start of the immunization series (either subcutaneous, intravenous or a combination of both routes). It was found that that a humoral response is induced in mice treated with both the conjugated and complexed binding agent. A so-called T2 cellular response to the binding agent was induced in these mice, but the T3 population (responsive to MUC1 or MUC1 peptide) was not obvious (T2 are Ab1 idiotype-specific T cells and T3 are Ab2 idiotype-specific T cells). A trend for reduction in tumor mass and size in mice treated with conjugated or complexed binding agent was also demonstrated, although statistical significance was not demonstrated in these studies.

EXAMPLE 9

Confirmatory Tumor Treatment Studies

Figure 1:
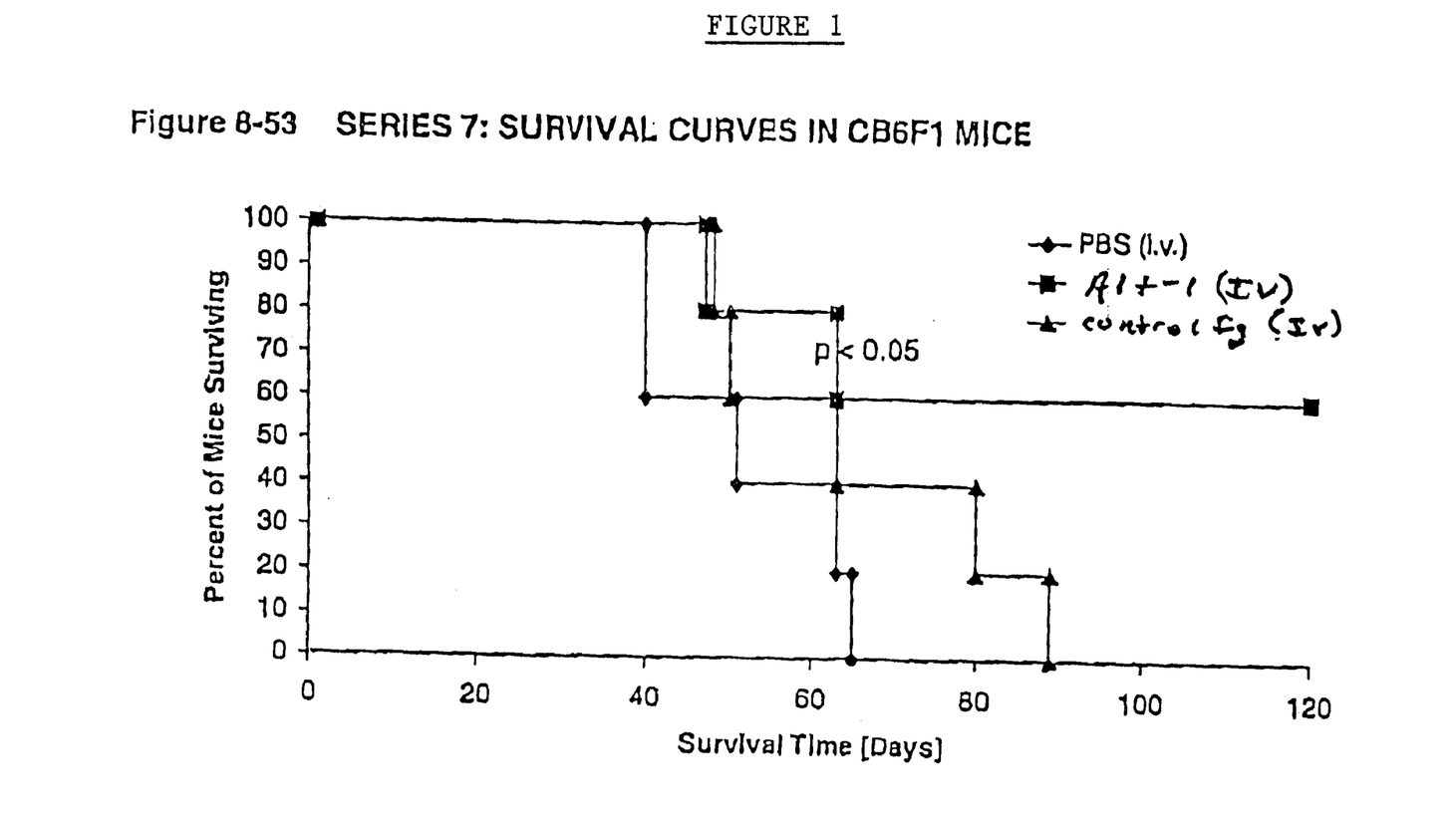
FIG. 1 shows results of a survival study of mice administered binding agents according to the invention and control mice.

Series 1 and 2 from the BALB/c mouse tumor model experiments were repeated in the CB6F1 tumor model. Ab2, Ab3 and T cell proliferation were again measured to determine humoral and cellular responses. The number of tumor foci occurring in the mice after injection of the various formulations was also assessed in one series and an estimate of tumor size was made by evaluating the uptake of $^{125}$I uridine in vivo. The last in this series of experiments evaluated the ability of binding agent according to Example 2 compared to control MAbs and PBS to affect the survival of mice implanted with the lung tumor model. In this confirmatory set of experiments, it appears that a humoral and a cellular response were induced in these mice, although no T cell response to MUC1 was observed. No significant reduction in tumor burden was observed, however, tumor size appeared to be reduced. There also appeared to be a survival advantage to mice injected with binding agent compared to those injected with control MAb or PBS. As shown in FIG. 1, there was significant improvement in the survival in mice treated with MAb-ALT-1 over mice treated with PBS. The p-value, determined in the Student's T test, for the treatment with MAB-ALT-1 over PBS treatment was <0.05. MAb-ALT-1, native antibody administered by intravenous injection, demonstrates anti-tumor effects in he MT-CB6F1 mouse tumor model. A minimum of three injections prior to inoculation of the tumor cells and four subsequent injections were necessary to demonstrate this effect, as previous experiments with fewer injections of the antibody were not as efficacious (data not shown).

EXAMPLE 10

Microsphere-encapsulated Binding Agent

Since liposomal formulations of antibodies can augment idiotypic responses, this study was performed to investigate the immune responses of microsphere-encapsulated binding agent administered to human breast tumor-bearing mice. Binding agent was incorporated into PLGA microspheres by a double-emulsion technique. Each BALB/c mouse received an inoculation of 5×10$^6$ 413BCR tumor cells subcutaneously on Study Day 0. One week later, the mice, in groups of 4 animals, were divided into the following treatment groups: PBS, IgG-KLH, binding agent-KLH, microspheres (MS), binding agent-Monophosphoryl Lipid A microspheres (MPLA-MS), and MUC-1. Sera were diluted to 1/100 and Ab2 and Ab3 responses were measured in ELISA prior to each immunization. Tumor volumes were measured with calipers in two dimensions every second day. Microsphere encapsulated binding agent induced a superior idiotypic immune response to that of binding agent conjugated with KLH or in complex with MUC-1. Microsphere encapsulated binding agent showed some suppression of tumor growth, but statistical significance not was achieved. This may be due to the fact that mice were not pre-immunized with the antibody in this experiment.

EXAMPLE 11

Specificity for Tumor-associated MUC-1

The biological disposition of $^{99m}$Tc-labeled binding agent was also determined through its administration to immunodeficient (nude) mice implanted with cultured human breast cancer (ZR-75- 1) cells. These cells have been previously tested and the expression of MUC1 antigen has been confirmed. The $^{99m}$Tc-labeled binding agent was injected intravenously (20 $\mu$Ci of $^{99m}$Tc on 20 $\mu$g of binding agent) and the animals were sacrificed at 3, 6 and 24 hours post injection as per standard protocol. The organs and tissues of interest were removed and assayed for radioactivity in a gamma counter. A second non-MUC1 reactive antibody of the same subclass ($^{99m}$Tc-labeled MOPC-21) was similarly tested in another group of animals at 6 and 24 hours post injection. The overall pattern of biodistribution between the two antibodies was similar for most organs with the exception of higher liver and spleen uptake for $^{99m}$Tc-labeled MOPC-21. This is most likely due to the higher amount of $^{99m}$Tc high molecular weight aggregates present in the preparation, and significantly higher uptake of $^{99m}$Tc-labeled binding agent in the tumor site. The difference in the mean tumor uptake of the two radiolabeled MAbs was analyzed using an unpaired two-tailed t-test and found to be statistically significant (p<0.001) at both 6 and 24 hours post injection. Therefore, the non-specific tissue localization of $^{99m}$Tc-labeled binding agent appears to be typical to that of other similarly prepared IgG$_1$ murine monoclonal antibodies. This uptake is representative of normal tissue accumulation processes, such as those associated with tracer distribution and antibody metabolism, and is reflected in the high liver, blood and kidney values respectively. The tumor uptake values represent an almost 5 fold increase in target tissue accumulation for the $^{99m}$Tc-labeled binding agent relative to the $^{99m}$Tc-labeled MOPC-2 1 preparation at 24 hours post injection. This highly significant difference is almost certainly indicative of preferential $^{99m}$Tc-labeled binding agent retention due to specific antigen binding within MUC1 expressing tumor xenograft tissue. This uptake resulted in a continuous rise of tumor to blood ratios with time and reaches a high of 2.1 at 24 hours. This is in comparison to a value of less than 1.0 for most other tissues (except for kidney at 1.5), implying active specific retention of the tracer.

EXAMPLE 12

Preferential Binding of Glycosylated MUC-1

ZR-75-1 cells, which express MUC-1 glycoprotein on their surface were deglycosylated by treatment with 4 mM Phenyl-N-α-D-Glucosamide at 37° C. for 48 hr. Binding of the binding agent according to Example 2 was compared for the untreated and deglycosylated MUC-1 by FACScan analysis using Alt-1 or a control antibody (SM3) known to bind an all peptide epitope of MUC-1. As shown in Table 1, there was a slight preference in binding for the untreated MUC-1. These results demonstrate that the binding agent binds an epitope that includes at least some carbohydrate.

| FACScan antibody | % positive cells; glycosylated MUC-1 | % positive cells; unglycosylated MUC-1 |
|---|---|---|
| PBS control | 6.23 | 6.76 |
| Alt-1 | 90.68 | 81.58 |
| SM3 | 7.49 | 41.26 |

EXAMPLE 13

Tumor Immunotherapy Using Xenogeneic Antibody

Figure 2:
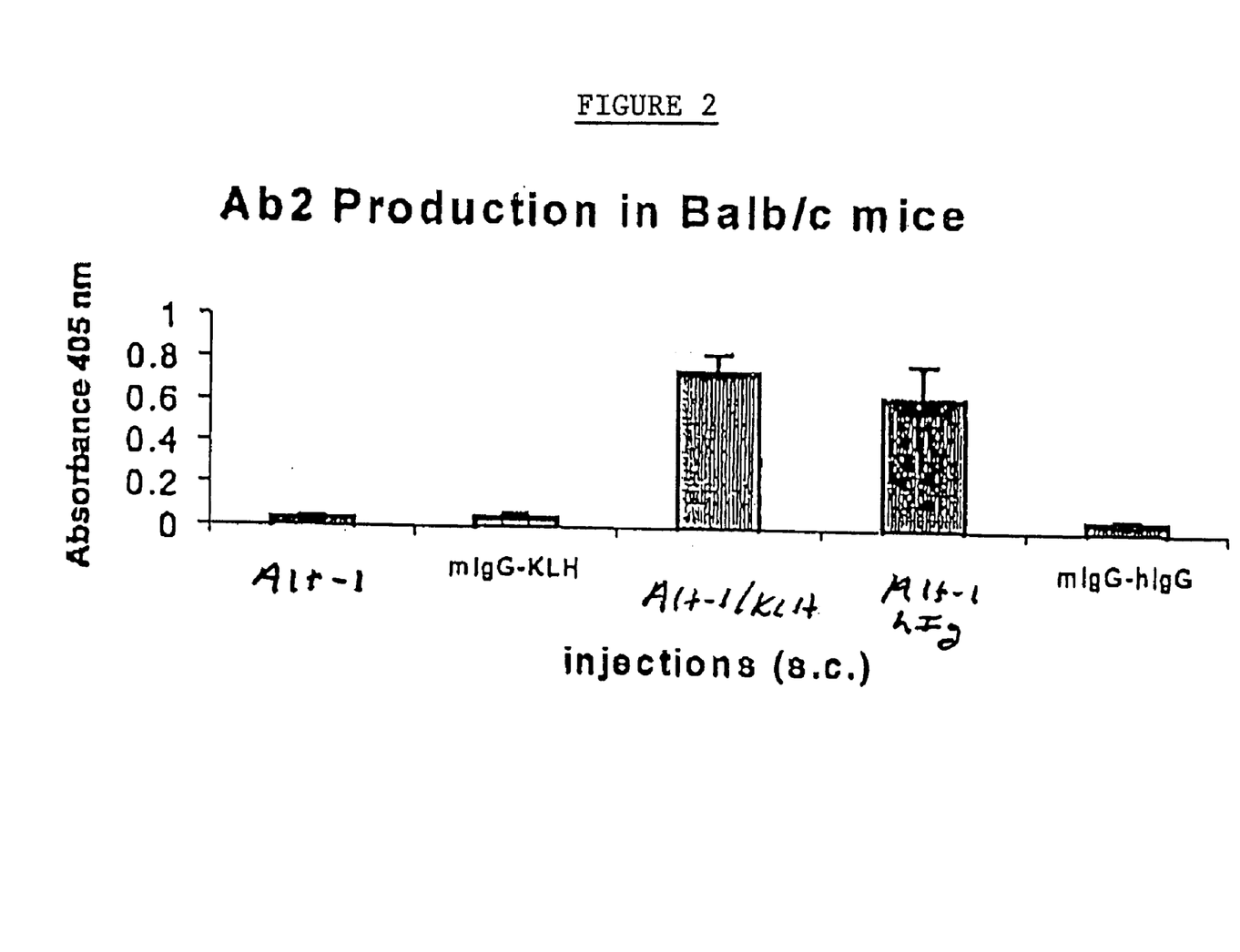
FIG. 2 shows results of studies of Ab2 production in mice administered binding agents according to the invention and control mice.
Figure 3:
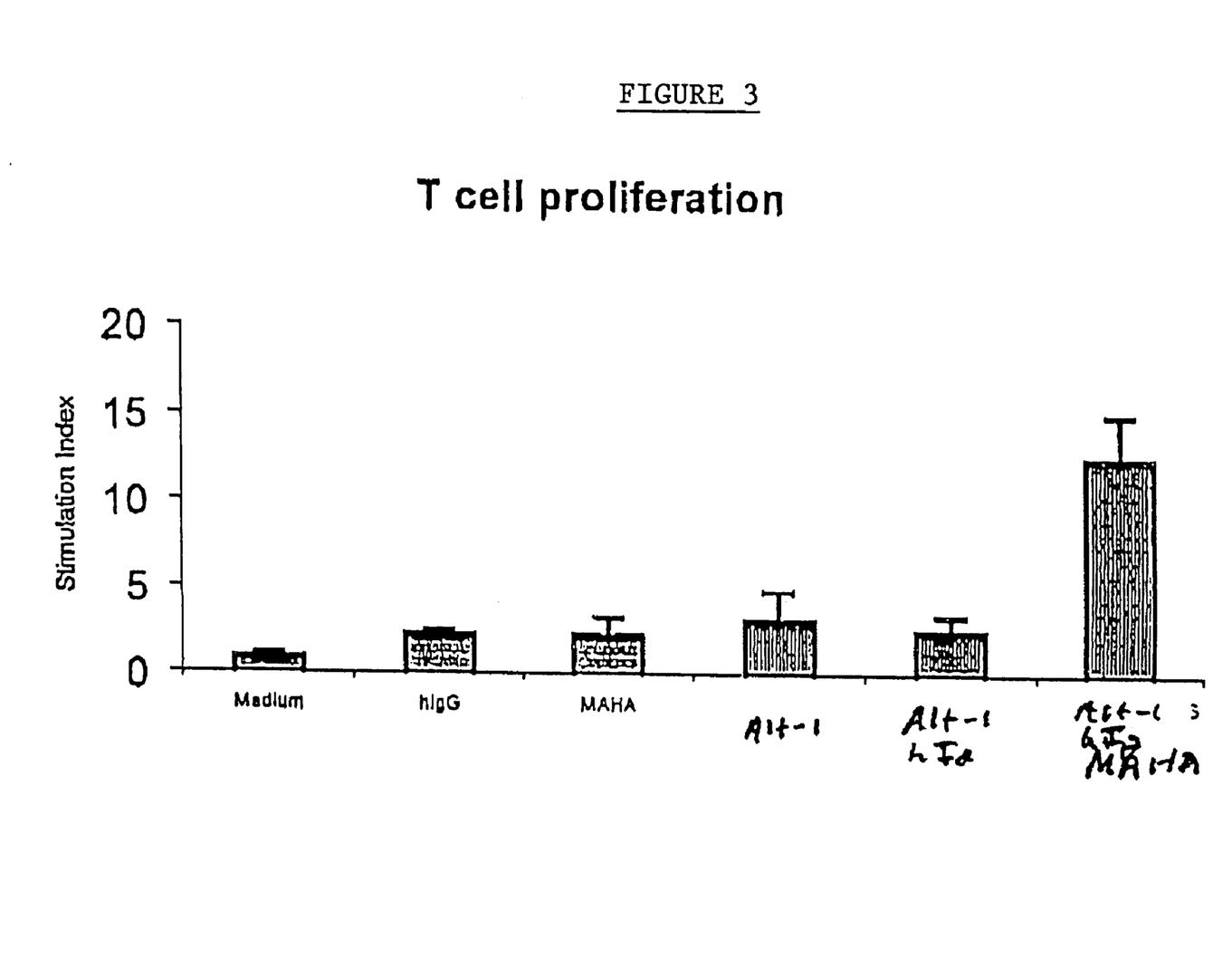
FIG. 3 shows results of studies showing that tumor cells can act as APCs to generate binding agent-specific T cell responses.

MUC-1 transfectant murine 413BCR tumor cells were inoculated into BALB/c mice. The mice were then injected five times (s.c.) with Alt-1 alone, or Alt-1 conjugated to KLH or hIgG. As controls, mouse IgG conjugated to KLH or hIgG was used. Immune responses were evaluated by measuring anti-idiotype antibodies (Ab2). For Ab2 detection, ELISA plates were coated with 100 μl Alt-1 F(ab)$_2$ (2.5 μg/ml) and incubated with diluted samples. Bound Ab2 was detected using anti-mouse IgG (Fc-specific) conjugated to HRP and ABTS. The results are shown in FIG. 2 as the mean absorbance at 405/492 nm+SD. These results show that Alt-1 presented in a xenogeneic context, or coupled with KLH results in production of Ab2, whereas neither Alt-1 nor the controls did. The ability of tumor cells to act as antigen-presenting cells to stimulate T-cells specific for Alt-1 was assessed as follows. 413BCR cells were incubated with PHA medium (positive control), Alt-1, hIgG, Alt-1 conjugated to hIgG, mouse anti-human antibodies (MAHA), or, Alt-1 conjugated to hIgG and mouse anti-human antibodies (MAHA) at 37° C. for 24 hours. Tumor cells were used as APC to stimulate purified T cells obtained from mice immunized with hIgG. T cell proliferation was measured using [$^3$H]-thymidine uptake. The results are shown in FIG. 3. Only the Alt-1 conjugated to hIgG and mouse anti-human antibodies (MAHA)-treated cells. These results indicate that when Alt-1 is presented in a xenogeneic context to tumor cells under conditions where the tumor cells can internalize it, the treated tumor cells can act as APCs to produce a T cell response specific for Alt-1.

Figure 4:
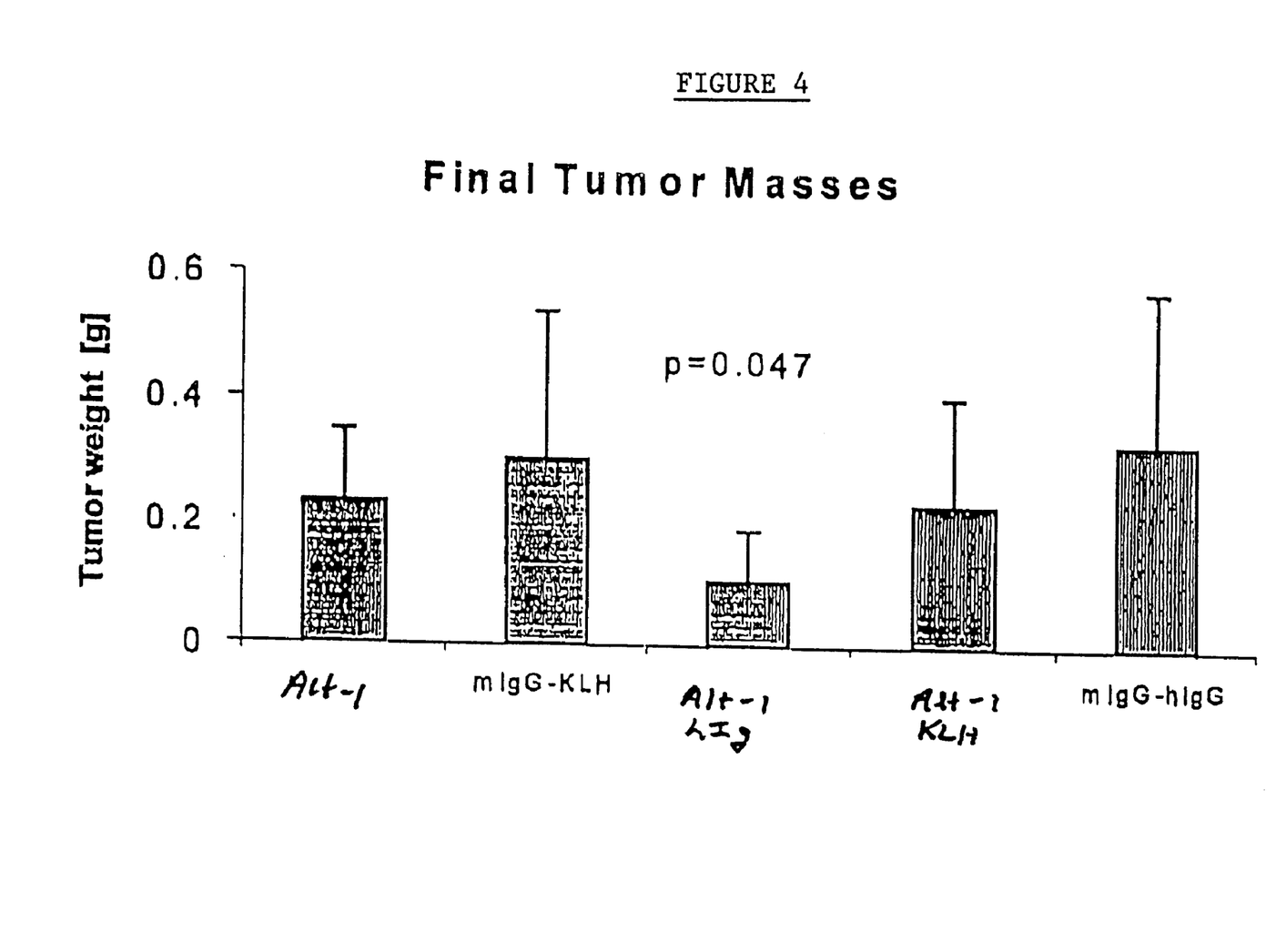
FIG. 4 shows results of tumor reduction studies of mice administered binding agents according to the invention and control mice.

Anti-cancer effects were evaluated by weighing tumor masses. 413BCR tumor-bearing mice were injected five times (s.c.) with different antibody formulations, as previously described. The mice were sacrificed at day 26, and the tumors were removed and weighed. The results are shown in FIG. 4 as mean +SD of tumors from 5 mice. Statistical analysis was conducted by t-test. These results show that Alt-1 presented in a xenogeneic context provides a statistical significant reduction in tumor load.

Taken together, these results show that binding agents according to the invention can produce both an anti-idiotypic and a cellular response, and that this response is effective in the treatment of tumors.

EXAMPLE 14

Treatment of hPBL-reconstituted Tumor-bearing SCID Mice

Figure 5:
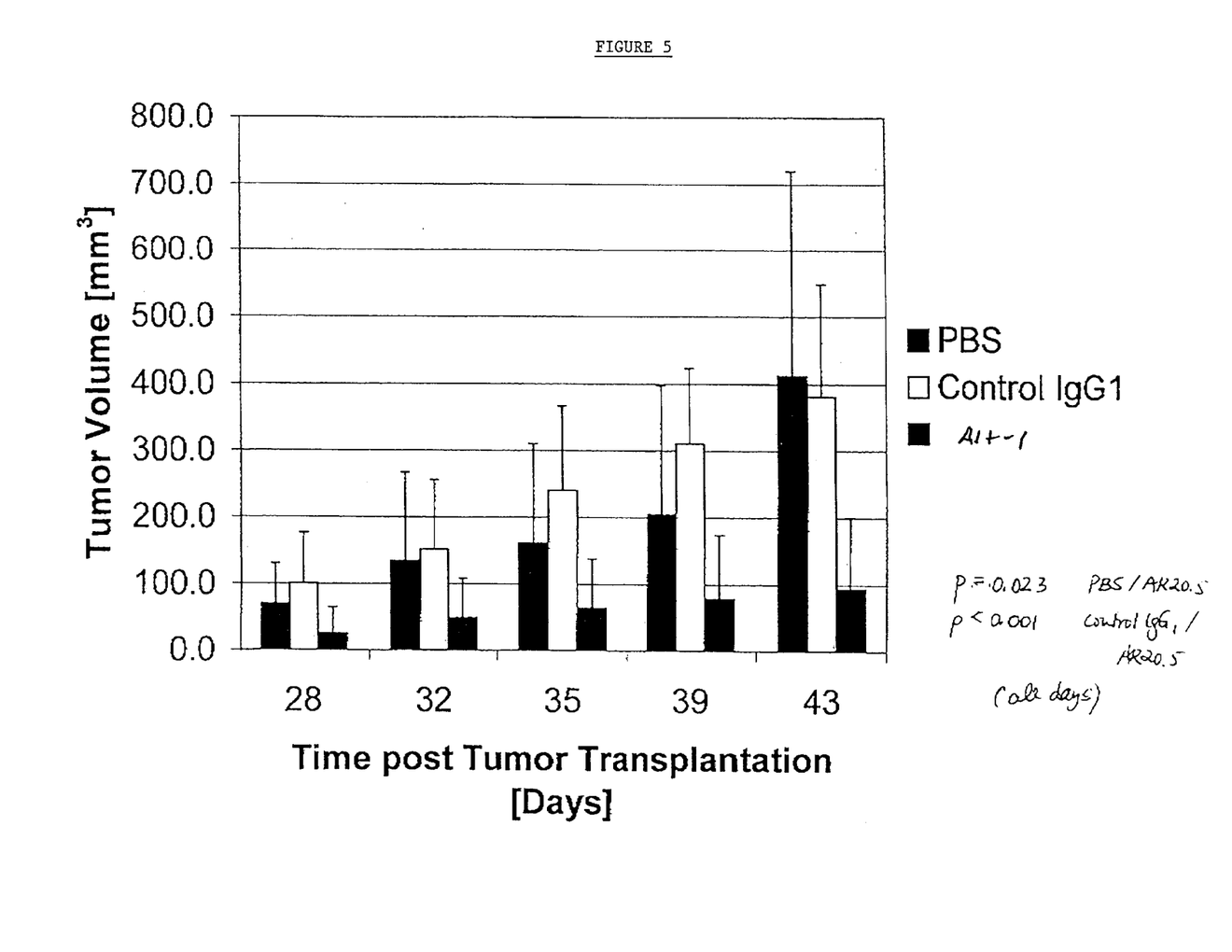
FIG. 5 shows results of tumor reduction studies of hPBL-reconstituted SCID mice administered binding agents according to the invention.

SCID/BG mice were injected with 10$^7$ hPBLs that had been stored at −80° C. Blood was collected from the mice on day 12 and tested for the presence of hIgG to determine if the mice were reconstituted. Five out of seven injected mice were reconstituted. Reconstituted mice were treated i.p. with PBS or 100 μg Alt-1 or a control IgG1 on day 0, with repeated treatments on days 7 and 14. On day 17, the mice were implanted s.c. with 5×10$^6$ tumor cells (NIH OVCAR-3)+20% matrigel. The mice were bled on day 21, and treated i.v. with PBS or 100 μg Alt-1 or a control IgG1 on days 21 and 38. Mice were sacrificed on days 28, 32, 35, 39 and 43 and their tumor volumes were measured. The results are shown in FIG. 5. These results demonstrate that xenogeneic binding agent Alt-1 provides statistically significant reduction in tumor volume even in the absence of any adjuvant or carrier protein.

EXAMPLE 15

Preparation of a Binding Agent Conjugated to Hypocrellin

The long circulating, sterically stabilized HBBA-R2 liposome (SL) and immunoliposome (SIL) formulations are composed of DPPC/maleimide-PEG2000-DSPE (94:6 molar ratio) and DSPC/Cholesterol/maleimide-PEG2000-DSPE (64:30:6 molar ratio) respectively. Control HBBA-R2 liposomes (CL) are composed of DPPC/DPPG (9:1 molar ratio). DSPC, DPPC, DPPG and Cholesterol were purchased from Avanti Polar Lipids (Alabaster, Ala., USA) and maleimide-PEG2000-DSPE was purchased from Shearwater Polymers Inc. (Huntsville, Ala., USA).

Synthesis of hypocrellins utilizes art-recognized procedures (see e.g., international application no. PCT/US98/00235). Two methods were used to load hypocrellins into liposomes. HBBA-R2 was either loaded into pre-formed SL and SIL by a solvent injection method at a 15:1 lipid to drug molar ratio or loaded into CL (15:1 lipid:drug) by a solvent dilution method.

For the solvent dilution method, the lipids and drug are first mixed together from stock solutions in organic solvent then dried. Methanol was added to give a final lipid concentration of 200 mM. Liposomes were formed when the lipid/drug solution was slowly diluted to 10 mM lipid at 65° C. with the addition of 500 μl aliquots of heated buffer (20 mM HEPES 140 mM NaCl, pH 7.4). The resulting liposomes were purified by gel filtration using Sephadex G50 and eluting with the above buffer.

For the solvent injection method, (HBBA-R2)-SL liposomes are first prepared by hydrating a dried thin film to a final concentration of 10 mM lipid 20 mM MOPSO 140 mM NaCl, pH 6.7. HBBA-R2 (10 mM in PEG300) is heated to 65° C. and injected, drop wise, into a 65° C. solution of liposomes, incubated for 15 minutes. The resulting hypocrellin-liposomes were extruded through 80 nm polycarbonate membranes using a Lipex Biomembranes (North Vancouver, BC) extrusion device to give an average vesicle size of 100 nm.

Immunoliposomes were produced as follows: The antibody was first dissolved in 20 mM pyrophosphate buffer (pH8.0) then incubated with 30 molar excess of 2-iminothiolane for 1 hour at 22° C. The thiolated antibody was purified and the pH lowered by gel chromatography using 20 mM MOPSO 140 mM NaCl, pH 6.7 buffer. The thiolated antibody was incubated at a concentration of 25–50 μgMAb/μmole lipid overnight at 22° C. with a portion of the maleimide-liposomes described above. Both sets of liposomes with and without bound antibody were purified by gel filtration, using Sepharose CL-4B and eluting with 20 mM HEPES 140 mM NaCl, pH 7.4 buffer. Approximately 90–95% of the antibody was bound to the liposomes.

The hypocrellin-liposomes solutions were concentrated using Sartorious AG. (Goettingen, Germany) Centrisart I centrifugal concentrators (300,000 MW cut-off). All liposome preparations are filter sterilized using Millex-GV 0.22 μm sterile filter units (Millipore Bedford, Mass. USA), assayed for lipid and drug concentrations then diluted to the desired concentration using sterile buffer (20 mM HEPES 140 mM NaCl, pH 7.4). The final lipid to drug molar ratio of 20:1 was typically obtained for all formulations.

The long circulating, sterically stabilized HBBA-R2 and HBEA-R1/2 liposome (SL) and immunoliposome (SIL) formulations are composed of DPPC/maleimide-PEG2000-DSPE (94:6 molar ratio) and DSPC/Cholesterol/maleimide-PEG2000-DSPE (64:30:6 molar ratio) respectively. Control HBBA-R2 liposomes (CL) are composed of DPPC/DPPG (9:1 molar ratio). DSPC, DPPC, DPPG and Cholesterol were purchased from Avanti Polar Lipids (Alabaster, Ala., USA) and maleimide-PEG2000-DSPE was purchased from Shearwater Polymers Inc. (Huntsville, Ala., USA).

Two methods were used to load hypocrellins into liposomes. HBBA-R2 was loaded into pre-formed SL and SIL by a solvent injection method at a 15:1 lipid to drug molar ratio. HBBA-R2 was loaded into CL (15:1 lipid:drug) and HBEA-R1/2 was loaded into SL and SIL (2:1 lipid:drug) by a solvent dilution method.

For the solvent injection method, liposomes are first prepared by hydrating a dried thin film, of various lipids, to a final concentration of 10 mM lipid with either 20 mM HEPES 140 mM NaCl, pH 7.4 for SL preps or 20 mM MOPSO 140 mM NaCl, pH 6.7 for SIL preps. The drug, dissolved in solvent (approx. 10–20 mM in methanol or approx. 5–10 mM in PEG300), is heated to 65° C. and injected, drop wise, into a 65° C. solution of liposomes.

For the solvent dilution method the lipids and drug are first mixed together from stock solutions in organic solvent then dried. Either methanol or PEG300 was then added to give a final lipid concentration of 200 mM or 50 mM respectively. Liposomes were formed when the lipid and drug solution was slowly diluted to 10 mM lipid at 65° C. with the addition of small aliquots of heated buffer (20 mM HEPES 140 mM NaCl, pH 7.4 for CL and SL preps or 20 mM MOPSO 140 mM NaCl, pH 6.7 for SIL preps).

The resulting hypocrelin-liposomes are extruded through 80 nm polycarbonate membranes using a Lipex Biomembranes (North Vancouver, BC) extrusion device to give an average vesicle size of 100 nm. The liposomes are then purified by gel filtration and assayed for lipid and drug concentrations. The final lipid to drug molar ratio of 20:1 was typically obtained for all formulations.

Immunoliposomes were produced as follows: The antibody was first dissolved in 20 mM pyrophosphate buffer (pH8.0) then incubated with 15–30 molar excess of 2-iminothiolane for 1 hour at 22° C. The thiolated antibody was purified and the pH lowered by gel chromatography using 20 mM MOPSO 140 mM NaCl, pH 6.7 buffer. The thiolated antibody was incubated at a concentration of 25–50 μgMAb/μmole lipid overnight at 22° C. with maleimide-liposomes (described above). Unbound antibody was removed by gel filtration, eluting with 20 mM HEPES 140 mM NaCl, pH 7.4 buffer. Approximately 90–95% of the antibody was bound to the liposomes.

If necessary, the hypocrellin-liposomes solutions were concentrated using Amicon, Inc (Beverly, Mass. USA) Centricon or Sartorious AG. (Goettingen, Germany) Centrisart I centrifugal concentrators (100,000 or 300,000 MW cut-off respectively).

EXAMPLE 16

Photodynamic Therapy in a Tumor-bearing Mouse Model

Figure 6:
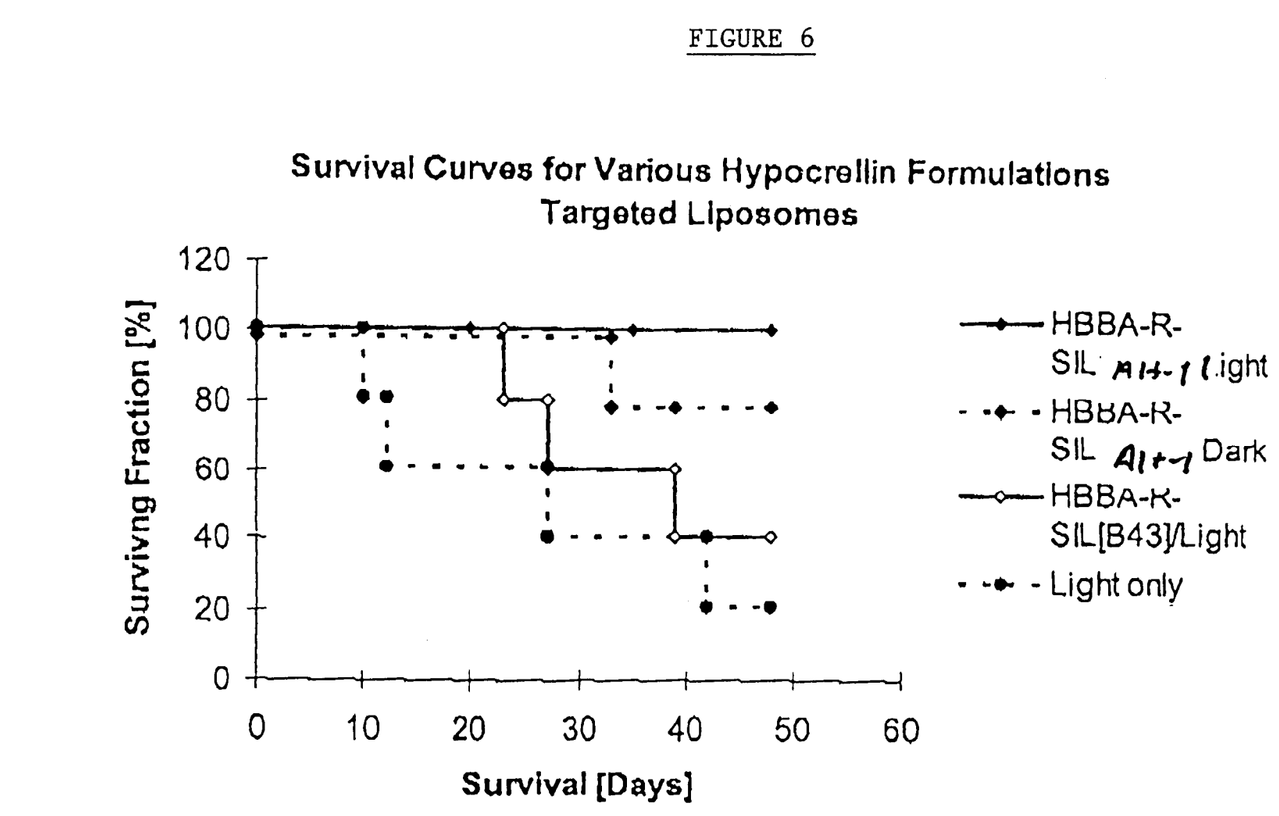
FIG. 6 shows results of tumor reduction studies using a binding agent of the invention coupled with a photodynamic agent.

BALB/c mice were injected with $2\times10^6$ 413BCR cells into the right flank s.c. Tumors appeared after 7–10 days. When tumors reached a diameter of about 5 mm, a conjugate according to Example 15, or a control liposome with drug, but a different IgG1, were injected i.v. at 1 mg/kg. Two hours later, mice were irradiated with a slide projector at >590 nm (red cut-off filter), 40 $J/cm^2$, 20 $mW/cm^2$. Control mice were not irradiated. The results are shown in FIG. 6. These results show that the conjugate according to the invention completely cures the tumor in the presence of light.

EXAMPLE 17

Mouse Tumor Survival Studies

CB6F1 mice were immunized three times before tumor implantation with Alt-1 binding agent, with PBS, with mouse IgG1 or with an unrelated mouse monoclonal antibody (50 μg in 0.2 ml PBS, i.v.). Mice were implanted with MT tumor cell line 410.4, a mouse breast cancer cell line transfected with full-length MUC-1 DNA. The tumor cells were injected i.v., $2\times10^5$ cells/mouse and developed metastases in the lungs. One week after tumor implantation, the mice were again immunized with Alt-1 binding agent, with mouse IgG1 or with an unrelated mouse monoclonal antibody (50 μg in 0.2 ml PBS). The mice were observed every other day for general condition changes, including weight, eyes and fur. The mice were euthanized if showing signs of being very sick or losing more than 25% of original weight.

The results are shown in the following table:

| Group | Mouse #1 | Mouse #2 | Mouse #3 | Mouse #4 | Mouse #5 | Median | Mean |
| --- | --- | --- | --- | --- | --- | --- | --- |
| PBS | 40 | 40 | 51 | 63 | 65 | 51 | 51.8 |
| MuIgG1 | 54 | 63 | 75 | 103 | 104 | 75 | 81.8 |
| unrel. | 48 | 50 | 63 | 80 | 89 | 63 | 66.0 |
| Alt-1 | 47 | 63 | 120 | 120 | 120 | 120 | 94.0 |

These results show that Alt-1 alone provides statistically significant protection from tumor cells expressing MUC-1 (P=0.038 against PBS; P=0.159 against unrelated antibody.

EXAMPLE 18

Establishment of HAMA Response in Human Patients

Seventeen patients were treated with Alt-1 antibody. Fourteen were female, of which eleven had breast cancer. Other cancers treated were thyroid (1), colon (2), endometrial (1), uterine (1) and salivary (1). Alt-1 was administered by intravenous infusion over 20–30 minutes at week 1, 3, 5, 9, 13 and 17. Dosing was in three cohorts, 1, 2 and 4 mg per patient. For the 1 mg cohort, 2 of 5 patients showed some increase in HAMA, one showed an increase to >200 ng/ml, and one showed an increase to over 2000 ng/ml. For the 2 mg cohort, all 5 patients showed some increase in HAMA, with two patients showing an increase >200 ng/ml and 1 patient showing an increase >2000 ng/ml. For the 4 mg cohort, 2 patients showed some increase in HAMA, both to >200 ng/ml. HAMA is taken as an indication of the extent of overall immune response generated against the antigen. Accordingly, these results suggest that as little as 1–2 mg of Alt-1 can induce a powerful immune response.

EXAMPLE 19

Reduction in Tumor-specific Antigen

Patients were treated as described in Example 18. Serial measurements of tumor antigen CA15.3 were obtained using a commercially available MUC-1 assay. The percent of patients who exhibited stabilization or reduction in CA15.3 levels included no patients at 1 mg Alt-1, 80% at 2 mg and 60% at 4 mg. Maximal reduction was observed for two patients in the 2 mg dose group who experienced 37% and 25% drops respectively.

EXAMPLE 20

Ab2 Formation

Patients were treated as described in Example 18. Levels of Ab2 were taken at the end of the study. Two patients in the 2 mg dose group had Ab2 levels >1240 U/ml and 1784 U/ml, respectively. One patient in the 4 mg dose group had Ab2 levels >1102 U/ml. The normal range is 0–200 U/ml.

EXAMPLE 21

Formation of Anti-MUC-1 Antibodies

Patients were treated as described in Example 18. Levels of anti-MUC-1 antibodies were taken at the end of the study. In the 2 mg dose group two patients exceeded the baseline value by >3x, at 667 U/ml and 2464 U/ml, respectively. Two patients from the 1 mg treatment group and one patient from the 4 mg dose group had anti-MUC-1 antibody levels 3x the baseline level. The normal level is 30–250 U/ml. Taken together, these data indicate that the 2 mg dose is probably optimal.

What is claimed is:

1. A binding agent that binds immunological determinants from amino acids residues of an epitope including carbohydrate and a peptide sequence consisting of the amino acid sequence DTRPAP (amino acid residues 3–8 of SEQ ID No. 2).

2. An antibody, wherein the antibody is Alt-1 produced by the hybridoma having ATCC No PTA-975.

3. A therapeutic composition comprising a binding agent selected from the group consisting of the binding agent according to claim 1, and Alt-1.

4. A therapeutic composition according to claim 3, wherein the binding agent is photoactivated.

5. A method for therapeutically treating a mammal bearing a tumor, the method comprising administering to the mammal an effective amount of a therapeutic composition of claim 3.

6. A method for therapeutically treating a mammal bearing a tumor, the method comprising administering to the mammal an effective amount of the therapeutic composition of claim 3, wherein the effective amount is a dosage of less than about 8 mg/30 kg body weight.

7. A method for therapeutically treating a mammal bearing a tumor, the method comprising intravenously administering to the mammal an effective amount of the therapeutic composition of claim 3.

8. A method for therapeutically treating a mammal bearing a tumor, the method comprising subcutaneously administering to the mammal an effective amount of the therapeutic composition of claim 3.

9. The method according to claim 5 or 6, wherein the binding agent is administered intravenously.

10. The method according to claim 5 or 6, wherein the binding agent is administered subcutaneously.

11. The method according to any of claims 5–8, wherein the effective amount is less than 8 mg/30 kg body weight.

12. The method according to claim 11, wherein the binding agent is administered at a dosage of less than about 3 mg/30 kg body weight.

13. The method according to claim 12, wherein the binding agent is administered at a dosage of about 2 mg/patient.

14. The method according to claim 12, wherein the binding agent is administered at a dosage of from about 0.5 to about 2 mg/30 kg body weight.

15. The method according to claim 14, wherein the binding agent is administered at a dosage of from about 0.5 to about 1.5 mg/30 kg body weight.

16. The method according to claim 15, wherein the binding agent is administered at a dosage of about 1 mg/30 kg body weight.

17. The method according to any one of claims 5–8, wherein the binding agent is administered at a dosage that is the maximum amount of binding agent that does not induce antibody-mediated toxicity.

18. The method according to any one of claims 5–8, wherein the binding agent is administered at a dosage that is the maximum amount of binding agent that does not produce ADCC or CDC.

19. The method according to any one of claims 5–8, wherein the binding agent is administered at a dosage that elicits a HAXA response >200 U/ml.

20. The method according to claim 19, wherein the binding agent is administered at a dosage that elicits a HAXA response >2000 U/ml.

21. The method according to claim 19, wherein the HAXA response is a HAMA response.

22. The method according to any one of claims 5–8, wherein the binding agent is administered at a dosage that reduces the level of tumor antigen CA15.3.

23. The method according to claim 7, wherein the binding agent is administered in the absence of an adjuvant.

24. The method according to claims 6 or 8, wherein the binding agent is administered in the presence of an adjuvant.

25. The method according to claim 20, further comprising irradiating the mammal with a visible light source.

26. The method according to claim 5, wherein the binding agent binds both circulating and tumor-bound MUC-1.

27. A method for therapeutically treating a mammal bearing a tumor, the method comprising administering to the mammal an effective amount of a therapeutic composition of claim 4.

28. The method according to claim 20, wherein the HAXA response is a HAMA response.

29. The method according to claim 28, wherein the binding agent is administered in the absence of an adjuvant.

* * * * *